Figure 1:
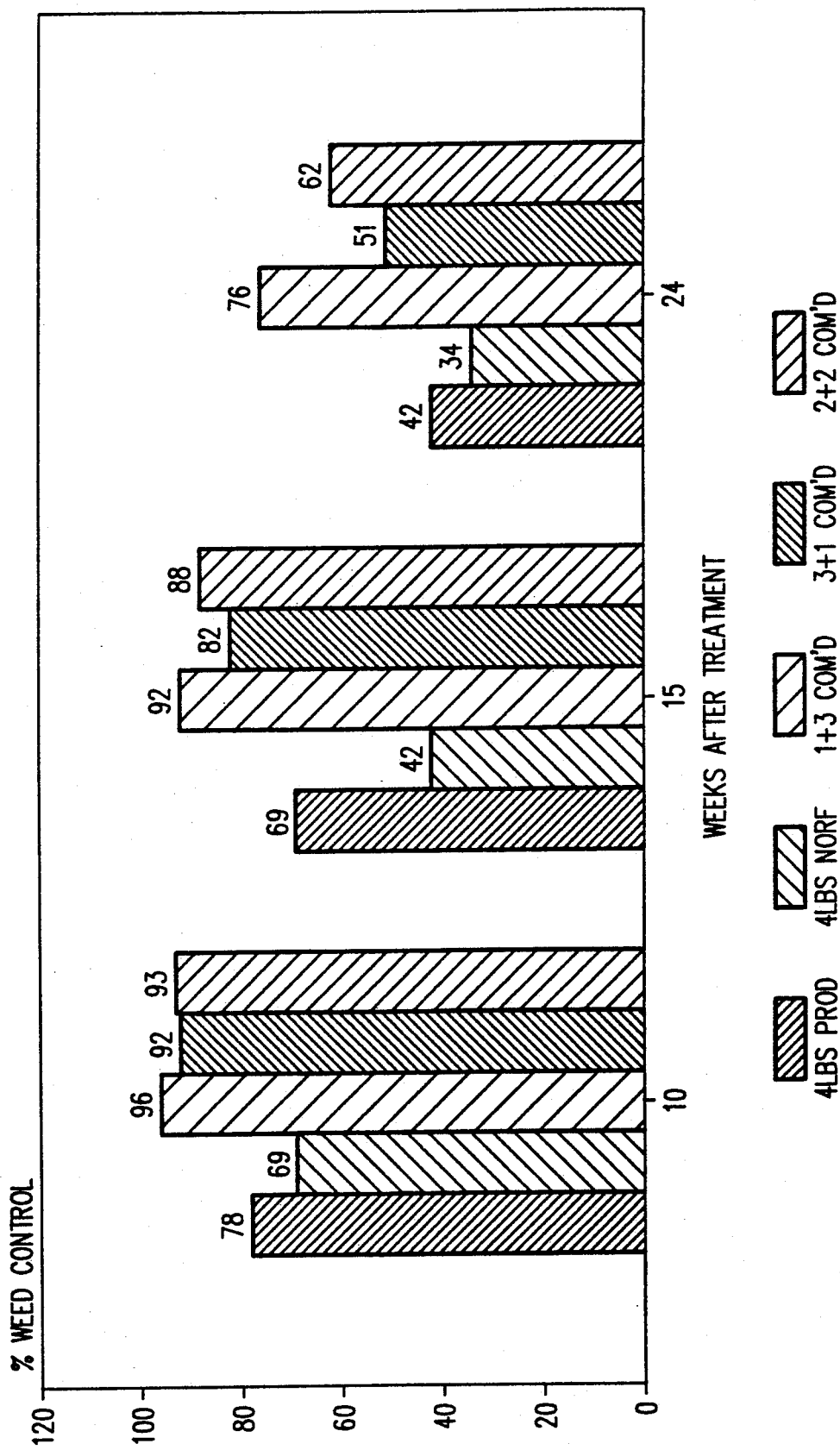

United States Patent [19]

Wilson et al.

[11] Patent Number: 5,108,484
[45] Date of Patent: Apr. 28, 1992

[54] NORFLURAZON AND A DINITROANILINE HERBICIDE IN COMBINATION FOR CONTROLLING UNWANTED PLANTS

[76] Inventors: Richard H. Wilson, 6014 Parkland Dr., Corpus Christi, Tex. 78413; Kevin T. Short, 407 Avenida De Mayo, Sarasota, Fla. 34242

[21] Appl. No.: 416,096

[22] Filed: Oct. 2, 1989

[51] Int. Cl.⁵ ............................................. A01N 43/58
[52] U.S. Cl. ......................................................... 71/92
[58] Field of Search ............................................ 71/92

[56] References Cited

U.S. PATENT DOCUMENTS 3,644,355  2/1972  Elner et al. ........................... 71/92 X
3,764,623 10/1973  Hunter et al. ........................ 564/441

OTHER PUBLICATIONS

Fisher, Chemical Abstracts, vol. 111 (1989) 110931x.

Primary Examiner—Richard L. Raymond
Attorney, Agent, or Firm—Allen E. Norris

[57] ABSTRACT

Combinations of phenylpyridazinone and dinitroaniline herbicides have synergistic effects.

10 Claims, 3 Drawing Sheets

NORFLURAZON AND A DINITROANILINE HERBICIDE IN COMBINATION FOR CONTROLLING UNWANTED PLANTS

The present invention concerns a method of controlling undesired plant growth employing co-application of a phenylpyridazinone herbicide such as norflurazon and a dinitroaniline herbicide such as prodiamine, herbicidal compositions comprising two such herbicides and the use of such compositions in controlling undesired plant growth.

Examples of suitable phenylpyridazinone herbicides (hereinafter PPO) include chloridazon and especially norflurazon.

Norflurazon, whose common name is 4-chloro-5-methyl-amino-2-(3-tri-fluoromethylphenyl)pyridazine-3-one, processes for its production, herbicidal compositions containing it and its use as a herbicide are described in U.S. Pat. Nos. 3,644,355 and 3,834,889, the contents of which are incorporated herein by reference. Norflurazon is available under the Registered Trademarks SOLICAM and ZORIAL.

Examples of suitable dinitroaniline herbicides (hereinafter DAH) include trifluralin, benfluralin, oryzalin, isopropalin and especially prodiamine.

Prodiamine whose common name is 2,6-dinitro-N',N'-dipropyl-4-trifluoromethyl-phenylenediamine, processes for its production, herbicidal compositions containing it and its use as a herbicide are described in U.S. Pat. Nos. 3,764,623 and 3,617,252, the contents of which are incorporated herein by reference.

It has now surprisingly been found that co-application of a PPO and a DAH results in better and longer-lasting control of undesired plant growth. This synergistic effect exhibits itself in a high degree of control at co-application ratios which are significantly lower than the rate of each individual compound required to obtain the same degree of control. Furthermore, at any given co-application rate the degree of control is higher than that obtained for the individual components at the same rate.

This synergistic effect allows for satisfactory control at reduced application rates for each component and even at levels which if employed for a particular component alone would give insufficient control. Additionally, longer residual control may be achieved. This provides for significant economic and environmental advantages in the use of PPOs and DAHs, and especially norflurazon and prodiamine.

Co-application can be achieved using tank mixes of preformulated individual active ingredients, simultaneous or sequential (preferably 1-2 days) application of such formulations or application of preformulated fixed pre-mix combinations of the individual active ingredients.

Co-application of PPOs and DAHs is particularly useful in controlling grasses, sedges and broadleaf weeds such as Elymus (wildrye) spp., Cynoda spp., e.g. bermuda grass (Cynodon dactylon), Cyperus spp., e.g. annual sedge (Cyperus compressus), Sorghum spp., e.g. johnson grass (sorghum halepense), Panicum spp., e.g. browntop panicum (Panicum fasciculatum), Portulaca spp., e.g. common purslane (Portulaca oleracea), Echinochloa spp., e.g. junglerice (Echinochloa colonum), Amaranthus spp., e.g. spiny pigweed (Amaranthus spinosus) and others known in the art (cf Crop Protection Chemical Reference 5th edition, pp 2135-8; 2144-5, John Wiley and Sons, NY). Co-application is particularly suited in crops such as alfalfa, ornamentals, and especially cotton, soybeans, vines, trees including e.g. top-fruit, pome fruit, store fruit, citrus and nuts and berries such as cranberries as well as in turf.

The combination of norflurazon and prodiamine is particularly useful for preemergent weed control.

The application rates of PPOs and DAHs employed in co-application will be course depend on the weed to be controlled, the crop plant involved, soil type, climate and various other factors. Optimum usage is readily determinable by one skilled in the art using routine testing such as greenhouse or small plot testing.

In general, for example, satisfactory results are obtained when coapplying norflurazon and prodiamine at rates of 0.1 to 6.0 lb/A especially 0.25 to 3.0 lb/A of each active ingredient. Especially preferred is 0.5 to 2.0 lb/A for each component.

In general, the weight ratio of the two components lies conveniently within the range of from 12:1 to 1:12, especially 4:1 to 1:4, particularly 3:1 to 1:3.

PPOs and DAHs when formulated individually or as preformulated fixed pre-mixes are conveniently employed in association with agriculturally acceptable diluents or carriers.

Methods of preparing herbicidal formulations are described in the literature along with suitable liquid and solid carriers such as in U.S. Pat. No. 4,192,669 and 4,163,661 which are incorporated herein by reference.

Suitable formulations contain from 0.01 to 99% by weight of active ingredient(s), and from 1 to 99.99% of solid or liquid diluent(s) and other additives e.g. surfactants. Higher rates of surfactant to active ingredient(s) are sometimes desirable and are achieved by incorporation into the formulation or at tank mixing. Application forms of a composition generally contain between 0.01 and 25 % by weight of active ingredient(s). Lower or higher levels of active ingredient(s) can, of course, be present depending on the intended use, the physical properties of the compound and the mode of application. Concentrate forms of a composition intended to be diluted before use generally contain between 2 and 90%, preferably between 5 and 81% by weight of active ingredient(s).

Useful formulations of the active ingredients either alone or in combination include dusts, granules, suspension concentrates, wettable powders, flowables and the like. They are obtained by conventional manner, e.g. by mixing an active ingredient(s) each optionally as twin packs with the diluent(s) and optionally with other ingredients.

Alternatively, the active ingredients may be used in micro-encapsulated form.

Agriculturally acceptable additives may be employed in the herbicidal compositions to improve the performance of the active ingredient and to reduce forming, caking and corrosion, for example.

"Surfactant" as used herein means an agriculturally acceptable material which imparts emulsifiability, spreading, wetting, dispersibility or other surface-modifying properties. Examples of surfactants are lignin sulfonates, and fatty and sulfates, e.g. lauryl sulfate, the condensation product of formaldehyde with naphthalene sulfonate, an alkylarylsulfonate, an ethoxylated alkylphenol, an ethoxylated fatty alcohol and the like.

"Diluent" as used herein means a liquid or solid agriculturally acceptable material used to dilute a concentrated material to a usable or desirable strength. For dusts or granules it can be e.g. talc. kaolin or diatomaceous earth, for liquid concentrate forms for example a hydrocarbon such as xylene or an alcohol such as isopropanol, and for liquid application forms e.g. diesel oil or preferably water.

For co-application commercially available forms of the active ingredients may be employed.

The compositions of the invention can also comprise other compounds having biological activity, e.g. compounds having similar or complementary herbicidal activity or compounds having antidotal, fungicidal, insecticidal, or insect attractant activity.

Solid forms for compositions are preferred from the point of view of environmentally innocuous packaging.

The following examples illustrate the practice of the present invention.

EXAMPLE 1

Formulated Pre-Mix

The herbicides are formulated in rates of 1.25 lbs. of norflurazon (1.0 lbs. active ingredient) plus 1.53 lbs. or prodiamine (1.0 lbs. active ingredient) as a dissolvable granular. The application is made by mixing the formulation in 20-30 gallons H20/acre and applying preemergent to weeds by a ground sprayer.

EXAMPLE 2

Field Test

Figure 2:
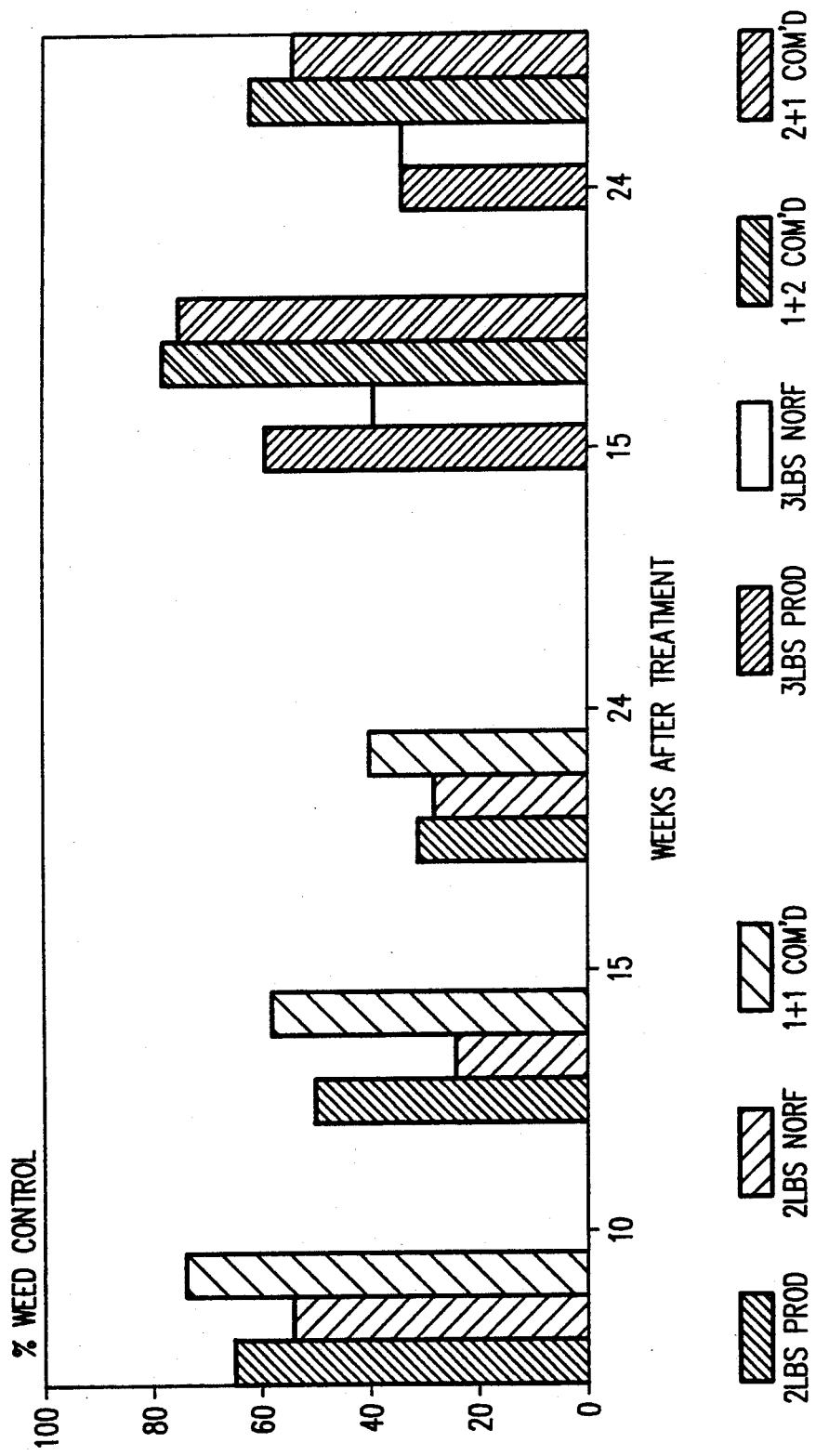
Figure 3:
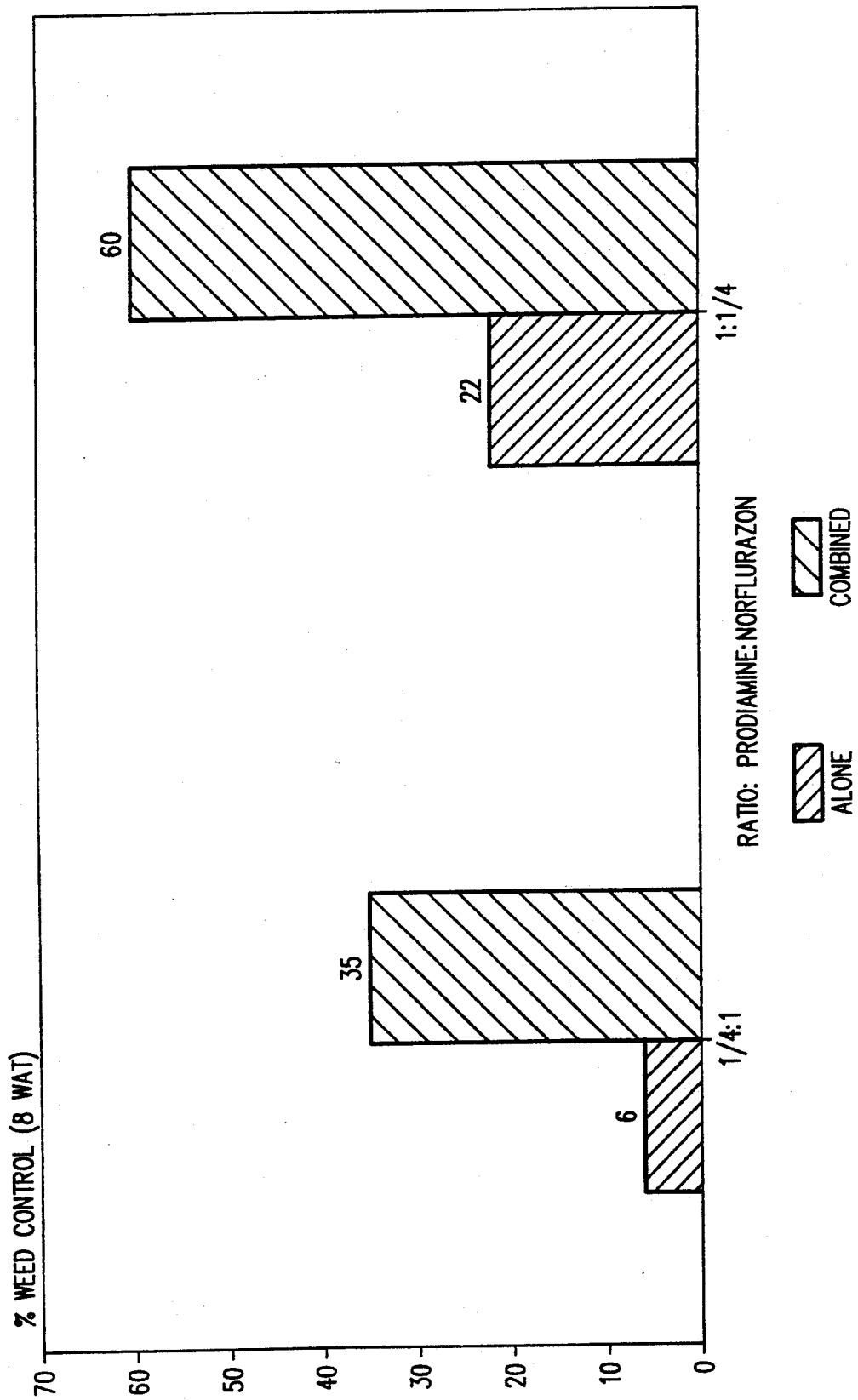

Herbicides were applied using $CO_2$ backpack sprayers to plots of Marrs Oranges as tank mixed spray solutions of indicated amounts of active ingredient in water (ca 26-31 gal/A). Application was preemergent. Separate evaluations of weed control for each treatment were made at the time intervals indicated. Each value is an average of 4 applications. The results are shown in FIGS. 1 and 2. The predominant weed was brown top panicum.

EXAMPLE 3

Field Test

The herbicide was applied using a $CO_2$ backpack sprayer preemergent to seeds in a fallow field. The applications involved 26 gallon $H_2O$/acre at 28 psi and used a 15 foot spray boom with 10 nozzles (8004 tips) 18" apart. Each value is the average of four (4) replications with purslane, Portulaca oleracea, the weed species evaluated for control. The results are shown in Table 3. Since norflurazon alone was without effect in controlling purslane, the control values for this wed and herbicide is not shown.

What is claimed is:

1. A method of controlling unwanted plant growth which comprises co-application to the locus of said undesired plant growth norflurazon and a dinitroaniline herbicide in herbicidally effective aggregate amount.

2. A method according to claim 1 wherein the dinitroaniline herbicide employed is prodiamine.

3. A method according to claim 2 wherein the amount of each of norflurazon and prodiamine is 0.1 to 6.0 lb/A.

4. A method according to claim 3 wherein the amount of each of norflurazon and prodiamine is 0.25 to 3.0 lb/A.

5. A method according to claim 4 wherein the amount of each of norflurazon and prodiamine is 0.5 to 2.0 lb/A.

6. A herbicidal composition comprising a herbicidally effective aggregate amount of norflurazon and a dinitroaniline herbicide.

7. A composition according to claim 6 wherein the dinitroaniline herbicide employed is prodiamine.

8. A herbicidal composition according to claim 7 wherein the ratio of weight of norflurazon to prodiamine is from 12:1 to 1:12.

9. A herbicidal composition according to claim 8 wherein the ratio of weight of norflurazon to prodiamine is from 4:1 to 1:4.

10. A herbicidal composition according to claim 9 wherein the ratio of weight of norflurazon to prodiamine is from 3:1 to 1:3.

* * * * *